(12) United States Patent
Barrett et al.

(10) Patent No.: US 11,147,612 B2
(45) Date of Patent: Oct. 19, 2021

(54) VAPORIZATION ELECTRODES AND ELECTROSURGICAL DEVICES EQUIPPED THEREWITH

(71) Applicant: endoMedical Concepts, Inc., Punto Gordo, FL (US)

(72) Inventors: Jon D. Barrett, Valparaiso, IN (US); Gregg Alan VanDusseldorp, Sr., Punto Gordo, FL (US); Gregg VanDusseldorp, II, Valparaiso, IN (US)

(73) Assignee: Endomedical Concepts, Inc., Punto Gordo, FL (US)

(*) Notice: Subject to any disclaimer, the term of this patent is extended or adjusted under 35 U.S.C. 154(b) by 244 days.

(21) Appl. No.: 16/405,504

(22) Filed: May 7, 2019

(65) Prior Publication Data

US 2019/0269453 A1 Sep. 5, 2019

Related U.S. Application Data

(62) Division of application No. 14/671,157, filed on Mar. 27, 2015, now Pat. No. 10,278,767.

(60) Provisional application No. 61/971,050, filed on Mar. 27, 2014.

(51) Int. Cl.
  *A61B 18/14* (2006.01)
  *A61B 18/00* (2006.01)

(52) U.S. Cl.
  CPC .... *A61B 18/14* (2013.01); *A61B 2018/00547* (2013.01); *A61B 2018/00577* (2013.01); *A61B 2018/00625* (2013.01); *A61B 2018/1417* (2013.01); *A61B 2018/1472* (2013.01)

(58) Field of Classification Search
  CPC .......... A61B 18/14; A61B 2018/00547; A61B 2018/00577; A61B 2018/00625; A61B 2018/1472
  See application file for complete search history.

(56) References Cited

U.S. PATENT DOCUMENTS

| | | | | |
|---|---|---|---|---|
| 5,354,296 A | * | 10/1994 | Turkel | A61B 18/1485 606/40 |
| 5,395,363 A | * | 3/1995 | Billings | A61B 18/1402 606/41 |
| 5,669,906 A | * | 9/1997 | Grossi | A61B 18/149 606/41 |
| 5,759,183 A | * | 6/1998 | VanDusseldorp | A61B 18/149 606/45 |
| 5,779,700 A | * | 7/1998 | Hahnen | A61B 18/149 606/46 |
| 5,827,274 A | * | 10/1998 | Bonnet | A61B 18/149 606/41 |
| 6,039,734 A | * | 3/2000 | Goble | A61B 18/12 606/41 |
| 6,197,025 B1 | * | 3/2001 | Grossi | A61B 18/14 606/41 |

(Continued)

*Primary Examiner* — Eric D. Bertram
(74) *Attorney, Agent, or Firm* — Hartman Global IP Law; Gary M. Hartman; Domenica N. S. Hartman

(57) ABSTRACT

Vaporization electrodes having functional surfaces with non-smooth semispherical shapes, and electrosurgical devices equipped therewith. The electrodes include a base oppositely disposed from its functional surface. The non-smooth semispherical shape of a functional surface is defined by a plurality of individual planar and/or cylindrical surfaces that intersect each other to define edges therebetween.

17 Claims, 3 Drawing Sheets

(56) References Cited

U.S. PATENT DOCUMENTS

| | | | |
|---|---|---|---|
| 6,277,114 B1* | 8/2001 | Bullivant | A61B 18/149 606/41 |
| 9,283,029 B2* | 3/2016 | Britva | A61B 18/1402 |
| 2002/0133148 A1* | 9/2002 | Daniel | A61B 18/1477 606/34 |
| 2008/0077129 A1* | 3/2008 | Van Wyk | A61B 18/149 606/46 |
| 2010/0152729 A1* | 6/2010 | Gallo, Sr. | A61B 18/148 606/41 |
| 2012/0232374 A1* | 9/2012 | Werneth | A61B 18/1492 600/393 |

* cited by examiner

VAPORIZATION ELECTRODES AND ELECTROSURGICAL DEVICES EQUIPPED THEREWITH

CROSS REFERENCE TO RELATED APPLICATIONS

This is a division patent application of U.S. patent application Ser. No. 14/671,157, filed Mar. 27, 2015, now U.S. Pat. No. 10,278,767, which claims the benefit of U.S. Provisional Application No. 61/971,050, filed Mar. 27, 2014. The contents of these prior applications are incorporated herein by reference.

BACKGROUND OF THE INVENTION

The present invention generally relates to surgical devices and components thereof. The invention particularly relates to vaporization electrodes adapted to vaporize biological tissue, for example, when treating benign prostatic hyperplasia by vaporizing prostate tissue in the afflicted urinary tract.

Benign prostatic hyperplasia (BPH), commonly known as enlarged prostate, is an increase in size of the prostate. BPH involves hyperplasia, an increase in the number of cells, rather than hypertrophy, an increase in cell size. If untreated, BPH can lead to partial or complete urinary tract obstruction, resulting in symptoms such as urinary frequency, urgency, or incontinence. Though not a form, precursor, or risk factor of cancer, BPH can lead to conditions such as urinary tract infection, retention, or insomnia. BPH affects about 6% of the world's males, and the risk of developing BPH increases greatly with increasing age.

The treatment of BPH can involve medication to combat both the urinary blockage as well as prostate enlargement, and involve minimally invasive therapies such as radiological operations. If these treatments fail, surgery may be performed. The most established minimally-invasive procedure is transurethral resection of the prostate (TURP), which involves removing part of the prostate through the urethra. TURP typically entails the use of surgical cutting loops or lasers to reshape and remove unwanted prostate tissue. An example is an electrosurgical probe disclosed in U.S. Pat. No. 8,167,878, whose entire contents are incorporated herein by reference. TURP procedures typically involve direct contact between a surgical instrument and prostate tissue, and may entail high operating temperatures.

Currently, vaporization treatments are viable alternatives that provide bloodless tissue ablation for patients with BPH. Vaporization treatments, such as transurethral vaporization of the prostate (TUVP), use plasma energy at relatively lower temperatures to remove tissue without directly contacting the tissue and while minimizing damage to surrounding healthy tissue. Vaporization treatments are conducted in an electrically conductive solution (e.g., saline), and utilize an instrument equipped with a vaporization electrode having a functional surface that is moved relative to the surface of tissue to vaporize the tissue. Current from the electrode's functional surface passes through the conductive solution to an associated return electrode (pole), which may be positioned in close proximity to the vaporization electrode (for example, mounted on the same instrument) or externally attached to a suitable location on the patient's body. Plasma is built up by the current flowing from the vaporization electrode through the conductive solution, and particularly over and around the functional surface of the vaporization electrode, such that the tissue is heated by the plasma and vaporized without the necessity of being directly contacted by the vaporization electrode.

Currently, vaporization electrodes exist having an electrode head having a smooth, spherical or semispherical shape on a functional surface disposed on one side of the electrode head, and a planar surface on the opposite side where feed conductors are connected to the electrode head. Because the plasma forms over and around the functional surface, the smooth, semispherical shape of the functional surface produces a semispherical vaporization effect on the tissue. The semispherical shape may facilitate producing a smooth current path back to the return electrode. However, a semispherical shape may also limit the ability to remove the intended tissue in an efficient, effective manner. As such, it would be advantageous to provide vaporization electrodes capable of vaporizing tissue without sacrificing smooth electrode current connection.

BRIEF DESCRIPTION OF THE INVENTION

The present invention provides vaporization electrodes suitable for vaporizing biological tissue, for example, when treating BPH. The electrodes comprise a functional surface that is not smooth, yet shaped in a manner that is preferably capable of improving tissue removal and energy efficiency, and preferably without sacrificing electrode current flow, plasma ignition, and usability. Generally, the electrodes have shapes that define a relatively wide or large base that narrows over the extent of the functional surface. The functional surface is not smooth, in that it comprises multiple surfaces that meet (intersect) to define multiple edges disposed within the functional surface, i.e., not simply at the perimeter of the functional surface.

According to one aspect of the invention, a vaporization electrode has a non-smooth semispherical shape and includes a base and a functional surface oppositely disposed from the base. The functional surface has a three-dimensional shape defined by a plurality of individual surfaces that intersect each other to define edges therebetween.

According to another aspect of the invention, an electrosurgical device includes at least one feed conductor and a vaporization electrode mounted to the feed conductor. The electrode includes a base and a functional surface oppositely disposed from the base, and the functional surface has a three-dimensional shape defined by a plurality of individual surfaces that intersect each other to define edges therebetween.

Electrodes of the types described above are believed to be particularly well suited for use in vaporization treatments that utilize plasma energy to provide bloodless tissue ablation, for example, for patients with BPH. Technical effects of the electrodes and methods of their use preferably include the ability of their functional surface to distribute current over a semispherical area adjacent the functional surface, while also concentrating the current within this semispherical area as a result of the edges within the functional surface. This concentration is believed to be capable of semicircular tissue removal, but in a more defined and concentrated manner. The non-smooth geometry of the functional surface is also believed to provide improved tissue removal with less required energy than an electrode having a conventional smooth functional surface. Additionally, the geometry of the functional surface is believed to promote smooth current flow from the vaporization electrode and instant plasma ignition consistent with existing vaporization electrode standards.

Other aspects and advantages of this invention will be further appreciated from the following detailed description.

BRIEF DESCRIPTION OF THE DRAWINGS

FIGS. 8 and 9 are side views of the electrode of FIGS. 6 and 7, wherein FIG. 8 is a side view of FIG. 6 and FIG. 9 is a side view of FIG. 7.

DETAILED DESCRIPTION OF THE INVENTION

Figure 1:
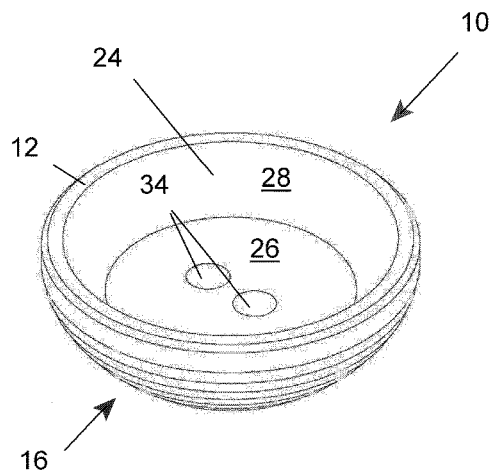
FIG. 1 is a perspective view of a plasma electrode in accordance with a first nonlimiting embodiment of the present invention.
Figure 2:
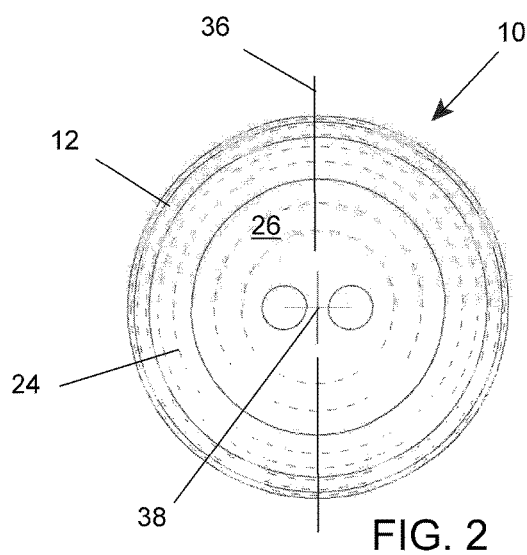
FIG. 2 is a top view showing a base of the electrode of FIG. 1.

FIGS. 1 through 9 represent vaporization electrodes 10 and 40 in accordance with nonlimiting embodiments of the invention. Each electrode 10 and 40 has a relatively wide base 12 and 42 that narrows toward an apex surface 14 and 44 to define a functional surface 16 and 46, respectively, having a three-dimensional shape. The functional surfaces 16 and 46 of the electrodes 10 and 40 are neither entirely planar nor smooth, but instead feature multiple surfaces that meet to define multiple edges, all within a roughly semispherical geometric shape or outline.

The electrode 10 of FIGS. 1 through 5 features a multistepped or multi-tiered functional surface 16 adapted to concentrate current over edges 22 defined by and between contiguous planar and arcuate surfaces 20a and 20b of adjacent steps or tiers 18. The electrode 40 of FIGS. 6 through 9 features a multi-faceted, semispherical functional surface 46 adapted to concentrate current over edges 42 defined by and between contiguous planar surfaces or facets 50 arranged in tiers 48. The vaporization electrodes 10 and 40 are suitable for use in tissue removal surgical procedures such as those employed in treating BPH. Various electrically-conductive materials can be used to form the electrodes 10 and 40. As evident from FIGS. 1 through 9, the functional surfaces 16 and 46 of each electrode 10 and 40 have non-smooth three-dimensional geometries that are each believed to promote tissue removal and energy efficiency without sacrificing electrode current flow, plasma ignition, and usability.

As evident from FIGS. 1 through 5, the base 12 of the electrode 10 is opposite the functional surface 16 and its apex surface 14, which is smaller in area than the base 12. In the represented embodiment, the apex surface 14 is parallel to the base 12 and perpendicular to the axis 38 of the electrode 10, though other configurations and orientations are possible, for example, the functional surface 16 could have one or more apices in the form of points or edges instead of a planar surface. The base 12 has a generally circular-shaped perimeter and is adapted for attachment to a feed conductor (80 in FIG. 10) for providing energy to the electrode 10. The surface of the base 12 is preferably electrically conductive, in other words, is not insulated with an electrically nonconductive coating or intermediate member. Methods of feed conductor connection and insulation in vaporization electrodes are well known to those of ordinary skill in the art, and all such methods are within the scope of the present invention.

Figure 3:
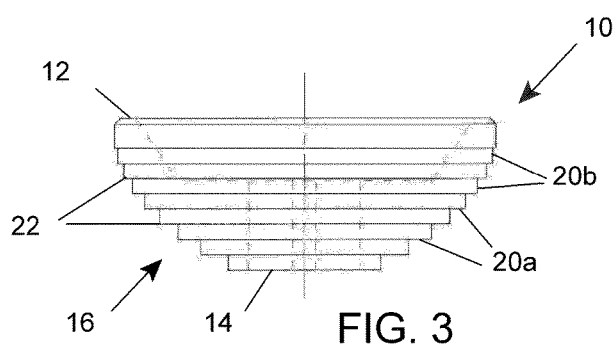
FIGS. 3 and 4 are side views of a functional surface of the electrode evidencing a plurality of substantially concentric planar steps or tiers that define the functional surface.
Figure 4:
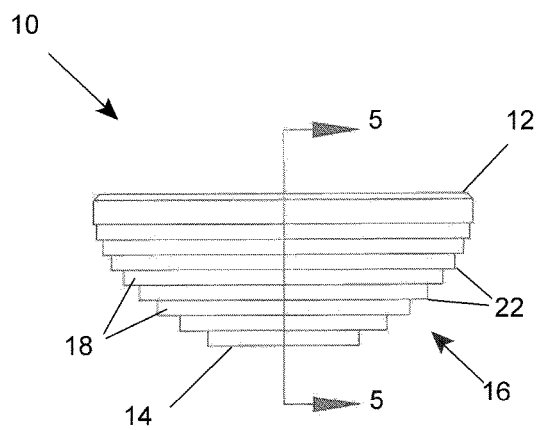
Figure 5:
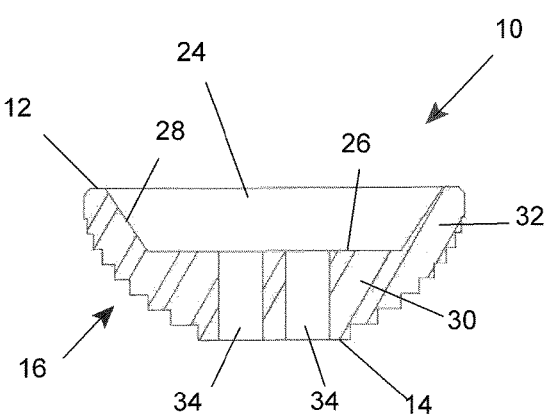
FIG. 5 represents a cross-sectional view along line 5-5 of FIG. 4.

Though bases with surfaces that are entirely planar are also within the scope of the invention, the base 12 shown in FIGS. 1 through 5 has a recess or cavity 24 defined therein. A beneficial aspect of the presence of the cavity 24 is to reduce the mass of the electrode 10, which is believed to promote faster plasma ignition. The cavity 24 defines a floor 26 recessed below the base 12, and a sloping annular-shaped surface 28 that surrounds and intersects the floor 26, and in turn the annular surface 28 is surrounded and intersected by the base 12. A base wall 30 is defined by and between the floor 26 of the cavity 24 and the functional surface 16, and a side wall 32 is defined by and between the annular-shaped surface 28 of the cavity 24 and the functional surface 16. The base wall 30 is represented in FIG. 5 as being thicker than the side wall 32. A pair of through-holes 34 are defined in the base wall 30 to facilitate connection to a pair of wires of the feed conductor 80. The holes 34 are represented as disposed on opposite sides of a plane of symmetry 36 of the electrode 10, and define openings in the apex surface 14. In preferred embodiments of the invention, the distal ends of the feed conductor 80 are typically flush or nearly flush with the apex surface 14 of the electrode 10, as evident from FIG. 10, so as not to protrude from the apex surface 14.

The multiple tiers 18, including a tier 18 that defines the apex surface 14 that forms the axially outmost extent of the electrode 10, define the three-dimensional shape of the functional surface 16. The tiers 18 are sized and shaped so as to contribute an axi-symmetrical shape to the functional surface 16, and converge at the apex surface 14 that will be disposed closest to the targeted tissue during use of the electrode 10. The tiers 18 are represented as having circular perimeters and concentric with each other about the axis 38 of the electrode 10. Each tier 18 is represented as having a planar surface 20a facing in an axial direction of the electrode 10 away from the base 12, and cylindrical-shaped surfaces 20b facing radially outward from the axis 38 of the electrode 10 so that each surface 20b surrounds and intersects one of the planar surfaces 20a to define therebetween one of the edges 22 of the functional surface 16. The surfaces 20a are roughly perpendicular to the axis 38 of the electrode 10 and the surfaces 20b are roughly parallel to the axis 38 of the electrode 10, such that the edges 22 generally define an included angle of about ninety degrees, though lesser and greater angles are also within the scope of the invention. As a result, the planar surface 20a of one tier 18 is roughly perpendicular to the cylindrical surface 20b of an adjacent tier 18, such that a sharp interior corner is defined between adjacent tiers 18 having an included angle of about ninety degrees. However, it is also within the scope of the invention that at least one of the sharp interior corners could be replaced by an interior filet, for example, such that the surfaces 20a and 20b of adjacent tiers 18 are arcuate portions of the filet, yet the surfaces 20a and 20b of the same tier 18 form an edge 22.

As evident from FIGS. 3 through 5, the axial dimensions of all but the first tier 18 (the axial dimensions of the surfaces 20b) may be substantially equal, with a typical but nonlimiting example being about 0.005 inch (about 0.13 mm). However, the diameters of the tiers 18 preferably decrease in a nonlinear manner toward the apex surface 14 of the functional surface 16, with the result that the radial dimensions of the tiers 18 (the radial dimensions of the surfaces 20a) gradually increase in a nonlinear manner with increasing distance from the base 12 (i.e., toward the apex surface 14). As nonlimiting examples, the radial dimensions of the surfaces 20a may nonlinearly increase from about 0.002 (about 0.05 mm) adjacent the base 12 to about 0.009 (about 0.23 mm) adjacent the apex surface 14. The resulting shape of the functional surface 16 can be seen in FIGS. 3, 4 and 5 as somewhat semispherical in outline, but not smooth due to the presence of the edges 22. Other suitable but nonlimiting dimensions for the electrode 10 include a diameter of about 0.125 inch (about 3.2 mm) at the base 12, a diameter of about 0.050 inch (about 1.3 mm) at the apex surface 14, and an axial length of about 0.050 inch (about 1.3 mm).

The circular shapes of the edges 22 and the juxtapositions of the edges 22 relative to each other (including the increasing radial distances between the edges 22 closer to the apex surface 14) are believed to provide certain advantages associated with the semispherical outline of the functional surface 16. In particular, current is believed to be concentrated along the edges 22 yet distributed over the functional surface 16, so that the surrounding plasma ignites in such a manner that provides concentrated and well-defined tissue removal. While the embodiment is shown in FIGS. 1 through 5 as having nine tiers 18 (including the tier 18 that forms the apex surface 14), fewer or more tiers 18 may be utilized. While not wishing to be held to any particular theory, increasing numbers of tiers 18 are believed to promote plasma ignition (as a result of the edges 22 defining additional paths back to an associated return electrode/pole) and provide a better tissue removal effect (as a result of increasing current density). As an example, it is believed that the electrode 10 preferably comprises at least four tiers 18 between the base 12 and apex surface 14.

Figure 8:
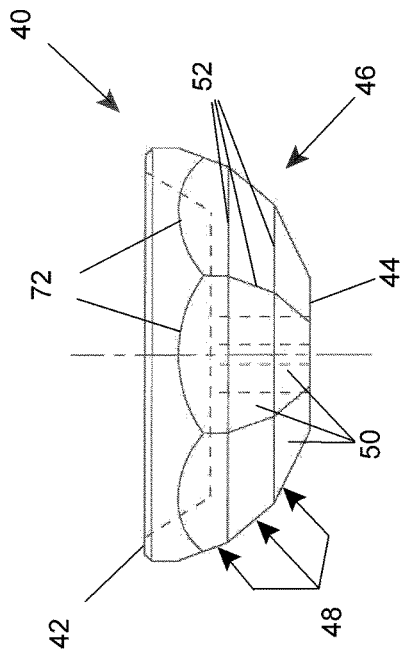
Figure 9:
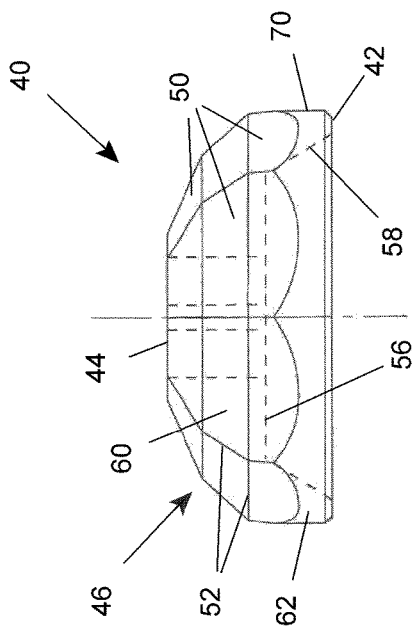
Figure 6:
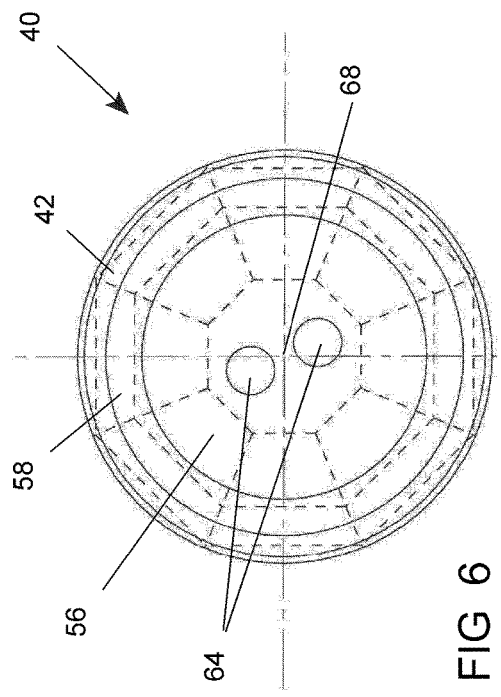
FIG. 6 is a top view of a plasma electrode in accordance with a second nonlimiting embodiment of the present invention.
Figure 7:
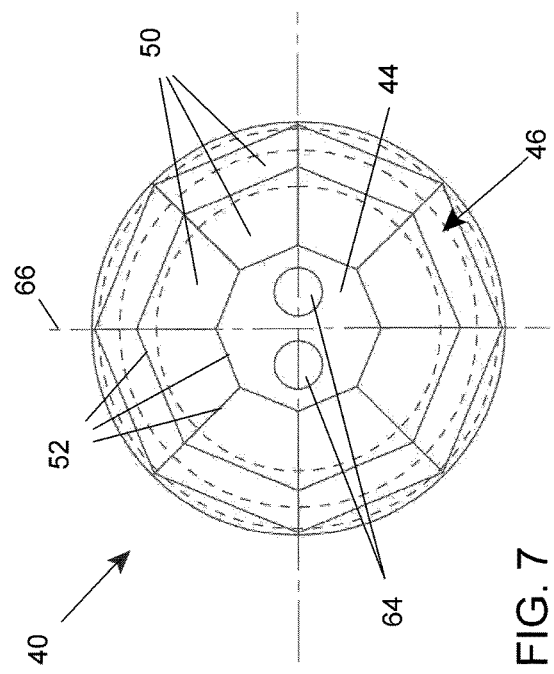
FIG. 7 is a bottom view showing a functional surface of the electrode of FIG. 6.

As evident from FIGS. 6 through 9, the electrode 40 shares similarities with the electrode 10 of FIGS. 1 through 5. For example, the base 42 of the electrode 40 is opposite its functional surface 46 and its apex surface 44, which is smaller in area than the base 42 and, in the represented embodiment, parallel to the base 42. In addition, the base 42 has a generally circular-shaped perimeter, is adapted for attachment to a feed conductor (80 in FIG. 10), and has a recess or cavity 54 defined therein. The cavity 54 defines a floor 56 recessed below the base 42, and a sloping annular surface 58 that surrounds and intersects the floor 56, and in turn the annular surface 58 is surrounded and intersected by the base 42. A base wall 60 is defined by and between the floor 56 of the cavity 54 and the functional surface 46, and a side wall 62 is defined by and between the annular surface 58 of the cavity 54 and the functional surface 46. The base wall 60 is represented in FIGS. 8 and 9 as being thicker than the side wall 62. A pair of through-holes 64 are defined in the base wall 60 to facilitate connection to a pair of wires of the feed conductor 80. The holes 64 are represented as disposed on opposite sides of a plane of symmetry 66 of the electrode 40, and define openings in the apex surface 44.

The functional surface 46 of the electrode 40 is defined by the multiple facets 50 that contribute a non-smooth and generally semispherical shape to the surface 46, somewhat resembling a cut gem. The facets 50 are shown as four-sided and arranged to define three concentric tiers 48, each containing eight facets 50. The tiers 48 are represented as concentric with each other about the axis 68 of the electrode 40. Each adjacent pair of facets 50 meets to define an edge 52, each represented in FIGS. 6 through 9 as being entirely linear. Facets 50 located in the tier 48 closest to the base 42 are represented in FIGS. 8 and 9 as intersecting a cylindrical-shaped outer wall 70 that surrounds the base 42, defining therewith arcuate edges 72. The facets 50 are sized and shaped so that the tiers 48 converge toward the apex surface 44, which will be disposed closest to the targeted tissue during use of the electrode 40. Current is concentrated along the facets 50 of the functional surface 46, and particularly along the edges 52 defined by contiguous facets 50, thereby promoting concentrated and well-defined tissue removal. While the embodiment is shown in FIGS. 6 through 9 as having twenty-five facets 50 (twenty-four of which are arranged to define the three concentric tiers 48), eight radial subsections, forty linear edges 52, and eight arcuate edges 72, the electrode 40 could comprise fewer or more facets 50, arranged in fewer or more tiers 48. However, as previously noted for the electrode 10 of FIGS. 1 through 6, the number of tiers 48 is believed to affect plasma ignition and tissue removal, and it is believed that the electrode 40 preferably comprises at least three tiers 48 between the base 42 and apex surface 44.

Other aspects or potential variations for the electrode 40 not discussed in any detail above can be, in terms of structure, function, materials, etc., essentially as was described for the electrode 10.

Figure 10:
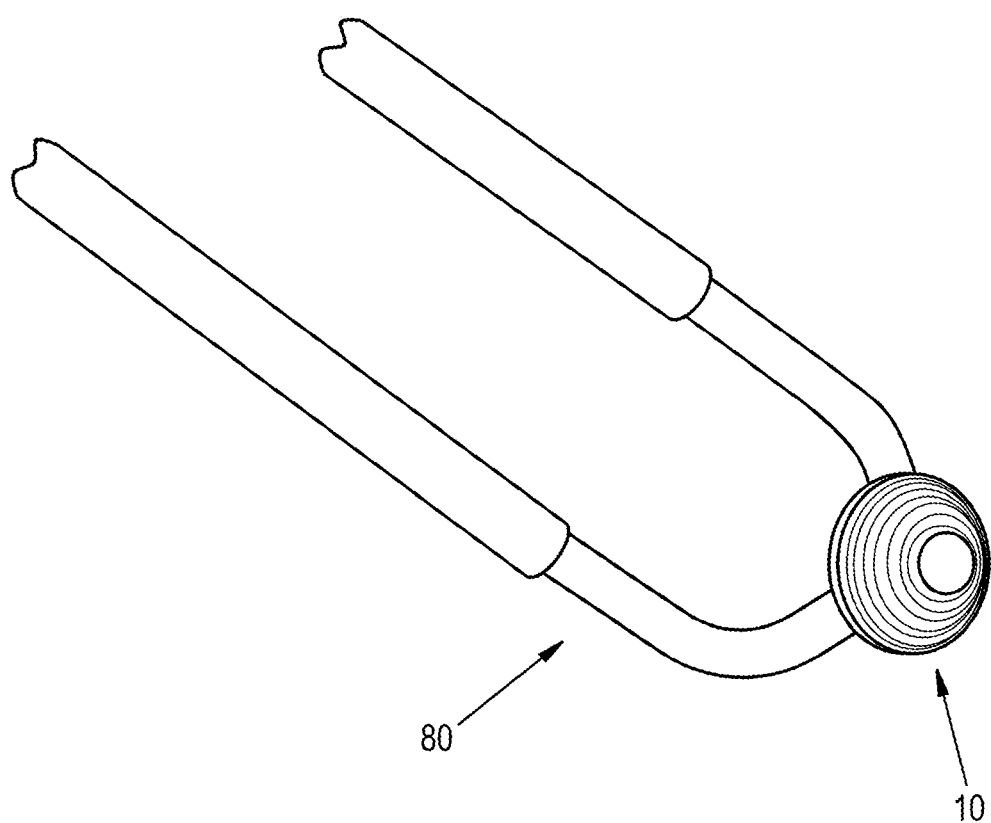
FIG. 10 is a perspective view representing the plasma electrode of FIGS. 1 through 5 mounted to an electrosurgical device (instrument or probe) in accordance with a nonlimiting embodiment of the present invention.

In use, the vaporization electrodes 10 and 40 are particularly well adapted to transfer radio frequency (RF) energy from an RF generator to biological tissue intended to be vaporized. For such a purpose, FIG. 10 shows the electrode 10 of FIGS. 1 through 6 mounted to feed conductors 80 of an electrosurgical device. Plasma builds up from current flow through an electrically conductive solution (e.g., saline) between the electrode 10 and a return electrode/pole (not shown), and particularly over and around the functional surface 16 of the electrode 10, such that tissue adjacent the electrode 10 is heated by the plasma and vaporized without being directly contacted by the electrode 10. The non-smooth, three-dimensional shapes of the functional surfaces 16 and 46 of the electrodes 10 and 40 are believed to concentrate current at particular locations on the surfaces 16 and 46, which is believed to promote ignition of the surrounding plasma such that tissue removal is provided in a more concentrated and well-defined manner. As a result, tissue can be removed more quickly and collateral damage to surrounding tissue can be minimized. In addition, current concentration can provide advantages in energy efficiency and plasma ignition.

In investigations leading to the present invention, the edges 22 and 52 of the electrodes 10 and 40 appeared to create points of current density that have a greater effect on de-bulking tissue while still producing a smooth surface after tissue was removed. Additionally, the non-smooth semispherical shapes of the functional surfaces 16 and 46 were believed to promote semispherical dispersion of energy which, in conjunction with appropriately positioning the functional surfaces 16 and 46 relative to the associated return electrode (pole), were concluded to promote optimal energy distribution and performance. The shapes of the electrodes 10 and 40 were further believed to achieve plasma ignition in a manner that created a pocket of vapor cushion between the electrode 10/40 and tissue by "igniting" the saline solution between the electrode 10/40 and tissue. In effect, the electrodes 10 and 40 hovered over the tissue and maintained tissue effect through plasma ignition. Generally, the performances of the non-smooth, semispherical shapes of the electrodes 10 and 40 were concluded to be attributable at least in part to their non-smooth semispherical shapes, in that RF current was believed to be better distributed over a semispherical area corresponding to the somewhat semispherical functional surfaces 16 and 46, and within this semispherical area current appeared to be concentrated along the edges 22 and 52 contained within the functional surfaces 16 and 46. The concentrated current enabled semicircular tissue removal similar to prior art smooth semispherical electrodes while using less energy, though in a more aggressive and concentrated manner. In view of the foregoing, the term "non-smooth semispherical shape" is defined herein as a shape that has a convex semispherical outline capable of promoting the distribution of energy over a semispherical area, but multiple edges are present within the convex semispherical outline to concentrate current within the semispherical area.

Though the invention has been described in reference to particular embodiments, these embodiments are nonlimiting examples of non-smooth, semispherical shapes within the scope of in this invention. Other possible embodiments are possible that contain the same or functionally similar non-smooth semispherical geometries comprising multiple edges and planar surfaces, and which are capable of providing the same or functionally similar advantages in tissue removal, efficiency, and usability. In addition, the dimensions of the planar surfaces of the electrodes 10 and 40 can be tailored to promote the desired aspects of the invention. Therefore, the scope of the invention is to be limited only by the following claims.

The invention claimed is:

1. A vaporization electrode comprising:
a base; and
a functional surface oppositely disposed from the base, the functional surface having a non-smooth semispherical shape defined by a plurality of individual surfaces that intersect each other to define edges therebetween, wherein the individual surfaces comprise planar surfaces and at least some of the edges are defined by intersections between the planar surfaces;
wherein the planar surfaces of the functional surface comprise multiple planar facets that intersect to define the edges therebetween;
wherein the multiple planar facets are arranged on the functional surface to define concentric annular-shaped tiers, and the edges are defined by and between the multiple planar facets within each of the tiers and by and between the multiple planar facets of adjacent pairs of the tiers.

2. The vaporization electrode according to claim 1, further comprising an apex surface farthest from the base and having a smaller area than the base.

3. The vaporization electrode according to claim 2, wherein the apex surface is planar and parallel to the base.

4. The vaporization electrode according to claim 1, wherein the tiers are concentric with an apex surface that is farthest from the base and has a smaller area than the base.

5. The vaporization electrode according to claim 4, wherein the apex surface has a non-circular periphery.

6. The vaporization electrode according to claim 1, wherein the base has a circular periphery.

7. The vaporization electrode according to claim 1, wherein the base has a recess defined therein.

8. The vaporization electrode according to claim 1, wherein the electrode is mounted to an electrosurgical device.

9. A vaporization electrode comprising:
a base; and
a functional surface oppositely disposed from the base, the functional surface having a non-smooth semispherical shape defined by a plurality of individual surfaces that intersect each other to define edges therebetween, wherein the individual surfaces comprise planar surfaces and at least some of the edges are defined by intersections between the planar surfaces; and
through-holes in the base to facilitate connection to a feed conductor of an electrosurgical device, the through-holes defining openings in an apex surface of the electrode that is farthest from the base and has a smaller area than the base.

10. A vaporization electrode attached to wires of a feed conductor of an electrosurgical device, the vaporization electrode comprising:
an axis;
a non-smooth shape defined by a functional surface converging toward an apex surface of the functional surface on the axis, the functional surface having a plurality of individual surfaces that intersect each other to define edges therebetween;
a base oppositely disposed from the functional surface and the apex surface thereof, parallel to the apex surface, and perpendicular to the axis, the electrode being configured so that the wires of the feed conductor are attached thereto at the base to provide energy to the functional surface; and
a cavity recessed beneath the base towards the apex surface;
wherein the individual surfaces of the functional surface comprise planar surfaces that are not perpendicular to the axis, face away from the base, and face radially outward from the axis, the planar surfaces are arranged to define concentric annular-shaped tiers that are concentric about the axis of the electrode, each of the tiers comprising a plurality of the planar surfaces;
the electrode being configured to attach the feed conductor at the base to provide energy to the functional surface and distribute the energy from the functional surface over a semispherical area.

11. The vaporization electrode according to claim 10, wherein the edges are defined by and between the planar surfaces within each of the tiers and by and between the planar surfaces of adjacent pairs of the tiers.

12. The vaporization electrode according to claim 10, wherein the apex surface has a smaller area than the base.

13. The vaporization electrode according to claim 10, wherein the apex surface is planar.

14. The vaporization electrode according to claim 10, wherein the planar surfaces of the functional surface comprise multiple planar facets that intersect to define the edges therebetween.

15. The vaporization electrode according to claim 10, wherein the apex surface has a non-circular periphery.

16. The vaporization electrode according to claim 10, wherein the base has a circular periphery.

17. The vaporization electrode according to claim 10, wherein the base has a recess defined therein, and the feed conductor of the electrosurgical device passes through the recess and is connected to through-holes in the apex surface.

* * * * *